United States Patent [19]

Mai et al.

[11] Patent Number: 4,551,526

[45] Date of Patent: Nov. 5, 1985

[54] SYNTHESIS OF ALPHA-AMINONITRILES

[75] Inventors: Khuong H. X. Mai; Ghanshyam Patil, both of Vernon Hills, Ill.

[73] Assignee: American Hospital Supply Corporation, Evanston, Ill.

[21] Appl. No.: 654,430

[22] Filed: Sep. 26, 1984

[51] Int. Cl.$^4$ .................. C07D 295/14; C07C 121/78
[52] U.S. Cl. ..................................... 544/163; 260/464; 260/465 D; 260/465 E; 260/465.5 R; 546/330; 548/342; 549/74; 549/492
[58] Field of Search ............... 260/465.5, 464, 465 E, 260/465 D; 556/417; 544/163; 546/330; 548/342; 549/74, 492

[56] References Cited

PUBLICATIONS

Gassman et al., Tetrahedron Letters, No. 40, pp. 3773–3776 (1978).
Stout et al., J. Org. Chem., vol. 48, 5369 (1983).
Ojima et al., Chemistry Letters, pp. 331–334, 737–740 (1975).

*Primary Examiner*—Dolph H. Torrence
*Attorney, Agent, or Firm*—Gildo E. Fato

[57] ABSTRACT

Described is a process for preparing alpha-aminonitriles having the formula

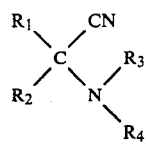

where $R_1$, $R_2$, $R_3$ and $R_4$ are each independently hydrogen, $C_1$–$C_{20}$ alkyl, $C_3$–$C_{12}$ cycloalkyl, $C_7$–$C_{15}$ aralkyl, unsubstituted or substituted aryl or heteroaryl or alternatively, $R_1$ and $R_2$ together with the carbon atom form a 3 to 12 member cycloalkyl group, or with a heteroatom form a 3 to 12 member heterocyclic group and $R_3$ and $R_4$ together with the nitrogen atom form a 3 to 12 member heterocyclic group and $R_3$ and $R_4$ together with the nitrogen atom form a 3 to 12 member heterocyclic group, optionally including oxygen, sulfur, or phosphorus as a second heteroatom, the process comprising: reacting an aldehyde or a ketone with trimethylsilyl cyanide (solvent is optional) to prepare alpha-trimethylsilyloxynitrile; reacting the silyloxynitrile so formed with an amine (or ammonia) in the presence of a lower-alkyl alcohol (or water) to prepare the desired alpha-aminonitrile.

The compounds so prepared are intermediates in the preparation of aminoacids.

6 Claims, No Drawings

SYNTHESIS OF ALPHA-AMINONITRILES

BACKGROUND OF THE INVENTION

Alpha-aminonitriles are important intermediates in the preparation of aminoacids, thiadiazoles and imidazole derivatives. A number of methods describing the preparation of alpha-aminonitriles are reported in the literature; but as yet, none provide a completely satisfactory procedure. See for example, W. L. Matier et al., J. Med. Chem. 16, 90 (1973); A. Strecker, Ann. 493, 20 (1932) and Y. Hamada et al., Tet. Lett., 4663 (1979). Most of the reported reactions involve lengthy reaction conditions and tedious work-ups. More recently, Ojima et al., Chem. Lett., 331 and 737 (1975), have shown that trimethylsilyl cyanide (TMSCN) reacts with ketimines to give the corresponding alpha-aminonitriles in excellent yield.

SUMMARY OF THE INVENTION

In accordance with one embodiment of the present invention, alpha-aminonitriles were prepared by reacting alpha-trimethylsilyloxynitriles with various amines in methanol. The silyloxynitriles were obtained by condensing a wide range of aldehydes (aliphatic, aromatic and heteroaromatic) with trimethylsilyl cyanide (TMSCN) in the presence of a catalytic amount of zinc iodide.

The process of the invention can be depicted by the following reaction scheme.

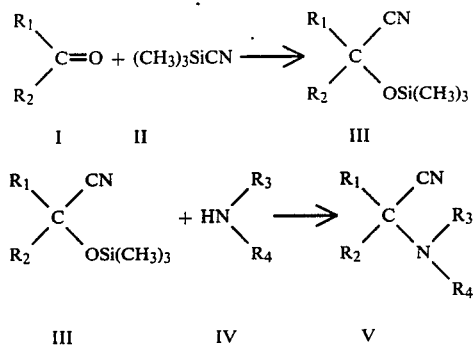

In the above formulae $R_1$, $R_2$, $R_3$ and $R_4$ are each independently hydrogen, $C_1$–$C_{20}$ alkyl, $C_3$–$C_{12}$ cycloalkyl, $C_7$–$C_{15}$ aralkyl, unsubstituted or substituted aryl or heteroaryl or $R_1$ and $R_2$ together with the carbon atom form a 6 member cycloalkyl group.

The term "alkyl" as used herein refers to straight or branched chain alkyl radicals containing from 1 to 20 carbon atoms including but not limited to methyl, ethyl, n-propyl, iso-propyl, n-butyl, sec-butyl, t-butyl, 2-methylhexyl, n-pentyl, 1-methylbutyl, 2,2-dimethylbutyl, 2-methylpentyl, 2,2-dimethylpropyl, n-hexyl, heptyl, octyl, nonyl, decyl, or eicosyl and the like.

The term "cycloalkyl" as used herein refers to cyclic saturated aliphatic radicals containing 3 to 12 carbon atoms in the ring, such as cyclopropyl, cyclobutyl, cyclopentyl, cyclohexyl, or cyclododecyl.

The term "aryl" represents phenyl or naphthyl which may be unsubstituted or substituted with loweralkyl of from one to about 6 carbon atoms, halo, hydroxy, amino, nitro, loweralkoxy, carboxy, loweralkanoyl, or loweralkoxycarbonyl.

"Heteroaryl" as used herein refers to radicals such as thiophene, furan, pyridine or imidazole, which may be unsubstituted or substituted.

"Substituted aryl or heteroaryl" as used herein refers to aryl or heteroaryl substituted with loweralkyl, loweralkoxy, carboloweralkoxy, amido, or halo.

In the process, a carbonyl (I) is reacted with trimethylsilyl cyanide (II) to provide an alpha-silyloxy nitrile. The reaction can be carried out by mixing the reactants in the presence of a catalyst such as zinc iodide, sodium iodide, potassium iodide, ammonium chloride or quaternary ammonium iodide. The reaction temperature is 0° to about 125° C., preferably 25° to 75° C. and the reaction time is several minutes to 24 hours, preferably 5 minutes to 2 hours. The reaction can be carried out without solvent, or if necessary, in a suitable aprotic solvent such as methylene chloride, chloroform, carbon tetrachloride, diethylether, tetrahydrofuran, dioxane, benzene, toluene, pentane, hexane, heptane, octane, acetonitrile, dimethylformamide and hexamethylphosphoramide.

The alpha-silyloxynitrile compound (III) is subsequently reacted with an amine (IV) to give the desired alpha-aminonitrile (V). The reaction can be carried out at room temperature, or at an elevated temperature, optionally under pressure, in a polar organic solvent such as water methanol, ethanol, propanol, butanol, phenol, dimethylformamide, hexamethylphosphoramide, dimethylsulfoxide, formic acid, acetic acid or a mixture thereof. The reaction temperature is usually about 25° to about 125° C. and the reaction period is about 5 minutes to 20 hours, preferably about 30 minutes to 2 hours.

In the described method, the primary amine (IV) may be theoretically used in an amount of about one equivalent for the purpose of preparing the alpha-aminonitrile (V) but it is preferable to use an excess amount of the amine (IV) which functions both as reactant and solvent.

DETAILED DESCRIPTION OF THE INVENTION

In accordance with one embodiment of the present invention, wherein compound I is an aldehyde, namely wherein $R_1$ is hydrogren, the preparation of alpha-aminonitriles from alpha-silyloxynitriles was conducted as follows.

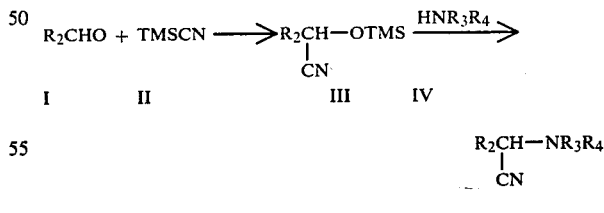

The alpha-silyloxynitrile III was prepared by the addition of TMSCN to aldehyde in the presence of catalytic amount of zinc iodide as described by Evans et al., J.C.S., Chem. Commun., 55 (1973), and Gassman et al., Tet. Lett., 3773 (1978). This reaction can be carried out neat or by using a solvent such as ether, tetrahydrofuran, methylene chloride or chloroform. Solvent was used only when the reaction was exceedingly exothermic or when the aldehyde was a solid. The subsequent amination produced alpha-aminonitriles V, a solvent such as an alcohol being required. It was found that the amination did not proceed in an aprotic medium. In contrast to the aqueous conditions of the classical Strecker synthesis, this reaction was carried under non-aqueous conditions. It is noted that the method worked particularly well with 2 or 2,6-disubstituted benzaldehydes as can be seen in Table I where the yields were considerably higher as compared to the literature methods.

TABLE I

α-Aminonitriles $$R_2CH-NR_3R_4 \cdot HCl$$
$$|$$
$$CN$$

| # | $R_2$ | $R_3$ | $R_4$ | Yield, %[a] ( )[b] | Mp, °C. |
|---|---|---|---|---|---|
| 1 | $C_2H_5$ | H | H | 91 (38)[1] | 144–6 |
| 2 | n-$C_6H_{13}$ | H | H | 83 | 147–9 |
| 3 | i-$C_4H_9$ | H | H | 95 | >225 |
| 4 | n-$C_4H_9C(Et)H$ | H | H | 87 (13)[1] | 131–2 |
| 5 | $C_6H_5CH_2$ | H | H | 99 (36)[1] | 173–5 |
| 6 | 2-$ClC_6H_4$ | H | H | 96 (24)[2] | 148–9 |
| 7 | 3-$ClC_6H_4$ | H | H | 97 (9)[2] | 175–6 |
| 8 | 4-$ClC_6H_4$ | H | H | 98 (16)[2] | 174–5 |
| 9 | 2,6-di$ClC_6H_3$ | H | H | 90 (27)[2] | 201–2 |
| 10 | 3-$MeOC_6H_4$ | H | H | 99 | 173–5 |
| 11 | 4-$MeC_6H_4$ | H | H | 96 | 175–6 |
| 12 | 4-$MeSC_6H_4$ | H | H | 97[c] | 106–7 |
| 13 | 4-$NCC_6H_4$ | H | H | 15 | 159–63 |
| 14 | 4-$MeO_2CC_6H_4$ | H | H | 77 | 177–9 |
| 15 | 2-Furyl | H | H | 94 | >200 |
| 16 | 2-Thienyl | H | H | 92 | 172–3 |
| 17 | 2-$ClC_6H_4$ | $C_6H_5CH_2$ | H | 94 (84)[2] | 155–6 |
| 18 | 2-$ClC_6H_4$ | $CH_3$ | $CH_3$ | 96[d] | 135–6 |
| 19 | 2-$ClC_6H_4$ | $(CH_2)_2O(CH_2)_2$ | | 93 | 175–6 |
| 20 | 2-$ClC_6H_4$ | $(CH_2)_4$ | | 91 | 147–9 |
| 21 | 3-$O_2NC_6H_4$ | $(CH_2)_4$ | | 95 | 168–71 |
| 22 | 3-$HOC_6H_4$ | $(CH_2)_4$ | | 87[e] | — |

[a] All compounds had correct elemental analyses and gave NMR and IR consistent with the structure listed.
[b] Values in parentheses are from the literature:
[1] Freifelder et al., J. Am. Chem. Soc. 83, 696 (1960).
[2] Matier et al., J. Med. Chem. 16, 901 (1973).
[c] Isolated as free amine.
[d] Due to its volatility, 5 fold excess dimethylamine was used.
[e] This compound is very hygroscopic, and therefore the mp was not taken.

A typical procedure is as follows: To a mixture of 3-chlorobenzaldehyde (5.6 g., 40 mmol) and TMSCN (5 g, 50 mmol) was added a catalytic amount of zinc iodide. After stirring for 15 minutes, a saturated solution of methanolic ammonia (30 mL) was added in one lot. The reaction mixture was warmed to 40° C. and stirred for 2 hours. After evaporation, the residue was taken up with ether, dried over MgSO₄ and filtered. Gaseous HCl was bubbled through the filtrate and the precipitated crude product was collected as an off-white powder, 8.1 g (97.0%), mp 175° C., NMR (CD₃OD) 5.95 (s,1H), 7.45–7.81 (m, 4H).

Similarly, compounds 17–22 were prepared, except that, after treating with methanol and an equivalent amount of amine, the mixture was refluxed for 2 hours.

The reaction is fairly general, although the substrates bearing an electron withdrawing group tend to give lower yield than those with an electron donating group.

The process can likewise be utilized in the preparation of alpha-aminonitriles from ketones. When the alpha-silyloxynitrile obtained from the ketone was treated with an amine, the resulting alpha-aminonitrile was isolated. On using ammonia, ketimine was found to be the major product (Table II).

TABLE II

Products of Amination of Alpha-Silyloxynitriles from Ketones

| Starting Materials | | Yield, % | |
|---|---|---|---|
| Ketone | Amine | Ketimine | Aminonitrile |
| Cyclohexanone | n-Propylamine | — | 50[a] |
| Cyclohexanone | NH₃ | 11 | 40[b] |
| Benzophenone | NH₃ | 70[d] | 5[c] |

[a] Isolated as oxalate salt, mp 127–30° C.
[b] Isolated as HCL salt, mp 210–2° C.
[c] Isolated as HCl salt, mp >200° C.
[d] A solution of alpha-trimethylsilyloxy-alpha, alpha-diphenylacetonitrile in methanolic ammonia was refluxed for 16 hours and worked up as usual. The solid was identified as alpha-amino-alpha, alpha-diphenylacetonitrile. HCl, mp >200° C. The filtrate was basified, dried over MgSO₄ and evaporated to an oil, which was distilled in vacuo to yield 70% of the ketimine.

What is claimed is:

1. A process of preparing an alpha-aminonitrile of the formula

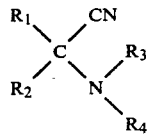

wherein $R_1$, $R_2$, $R_3$ and $R_4$ are each independently hydrogen, $C_1$–$C_{20}$ alkyl, $C_3$–$C_{12}$ cycloalkyl, $C_7$–$C_{15}$ aralkyl, a phenyl or naphthyl group which may be unsubstituted or substituted with loweralkyl of from 1 to 6 carbon atoms, halo, hydroxy, amino, nitro, loweralkoxy, carboxy, loweralkanoyl, or loweralkoxy-carbonyl, thiophene, furan, pyridine or imidazole, or $R_1$ and $R_2$ together with the carbon atom to which they are attached form a 6 member cycloalkyl group, which process comprises:

reacting a compound of the formula

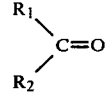

with trimethylsilyl cyanide in the presence of a catalytic amount of a catalyst selected from the group consisting of an alkali metal iodide, zinc iodide, quaternary ammonium iodide or ammonium chloride, and subsequently reacting the alpha-trimethylsilyloxynitrile so formed with an amine selected to produce the desired alpha-aminonitrile.

2. The process of claim 1 wherein the compound $R_1R_2C=O$ is reacted with trimethylsilyl cyanide at a temperature of from about 0° C. to about 125° C. for a time of up to about 24 hours.

3. The process of claim 2 wherein the reaction is carried out either without a solvent or in the presence of a suitable aprotic solvent.

4. The process of claim 3 wherein the aprotic solvent is selected from the group consisting of methylene chloride, chloroform, carbon tetrachloride, diethylether, tetrahydrofuran, dioxane, benzene, toluene, pentane, hexane, heptane, octane, acetonitrile, dimethylformamide or hexamethylphosphoramide.

5. The process of claim 1 wherein the alpha-siloxynitrile is reacted with the amine in a polar organic solvent and at a temperature of from about 25° C. to about 125° C. and from a time of about 5 minutes to about 20 hours.

6. The process of claim 5 wherein the polar solvent is selected from the group consisting of water, methanol, ethanol, propanol, butanol, phenol, dimethylformamide, hexamethylphosphoramide, dimethylsulfoxide, formic acid, acetic acid, or a mixture thereof.

* * * * *